United States Patent [19]

Bernhagen et al.

[11] 4,317,945

[45] Mar. 2, 1982

[54] PROCESS FOR PREPARING 2-METHYL-2-SEC.BUTYL-1,3-PROPANEDIOL

[75] Inventors: Wolfgang Bernhagen, Mulheim an der Ruhr; Jürgen Weber, Oberhausen; Helmut Bahrmann, Hünxe; Helmut Springer, Oberhausen, all of Fed. Rep. of Germany

[73] Assignee: Ruhrchemie Aktiengesellschaft, Oberhausen, Fed. Rep. of Germany

[21] Appl. No.: 178,396

[22] Filed: Aug. 15, 1980

[30] Foreign Application Priority Data

Aug. 22, 1979 [DE] Fed. Rep. of Germany ....... 2933919

[51] Int. Cl.$^3$ .................. C07C 29/14; C07C 31/20
[52] U.S. Cl. ........................... 568/853; 568/448; 568/461; 568/462
[58] Field of Search ........................................ 568/853

[56] References Cited

U.S. PATENT DOCUMENTS

| | | | |
|---|---|---|---|
| 2,413,803 | 1/1947 | Tribit | 568/853 |
| 2,761,881 | 9/1956 | Rosin | 568/853 |

FOREIGN PATENT DOCUMENTS 730734  3/1966  Canada ............................... 568/853

*Primary Examiner*—Joseph E. Evans
*Attorney, Agent, or Firm*—Bierman & Bierman

[57] ABSTRACT

A process for the preparation of 2-methyl-2-sec.butyl-1,3-propanediol comprising hydroformylating 2-methyl-1-butene with carbon monoxide and hydrogen in the presence of a first catalyst to form the substance 3-methyl-pentanal, condensing said substance with formaldehyde, or a compound which forms formaldehyde under the conditions of condensation in a basic medium to form alpha-sec.butyl-acrolein, partially hydrogenating said acrolein in the presence of a second catalyst to form the material 2,3-dimethyl pentanal, and converting said material into said diol by treatment with formaldehyde, or a compound which forms formaldehyde under the conditions of conversion, in the presence of a strong base as a third catalyst.

The compound of the present invention is useful as an intermediate in the production of pharmaceuticals and drugs; in particular, the production of carbamates which are useful as tranquilizers and blood pressure lowering agents.

18 Claims, No Drawings

PROCESS FOR PREPARING 2-METHYL-2-SEC.BUTYL-1,3-PROPANEDIOL

This application claims the benefit of the priority of German Application Ser. No. 29 33 919.3, filed Aug. 22, 1979.

The present invention is directed to the preparation of certain intermediates which are useful in the production of drugs and pharmaceuticals. More specifically, it is directed to a process for the preparation of 2-methyl-2-sec.butyl-1,3-propanediol from 2-methyl-1-butene. The intermediate which is the object of the present process is used for the manufacture of the carbamates which act as tranquilizers and blood pressure lowering agents.

There are a number of processes which are known for the production of this diol. In U.S. Pat. No. 2,937,119, the compound is produced by the reduction of diethyl sec.-butyl-methyl-malonate with lithium aluminum hydride. However, this reaction produces a very impure product.

Another process is described in Farmaco (Pavia) Ed. Sci. 18 (10) 780-92 (1963). This 6-stage process starts with 1-methoxypropanol-(2). This compound is dehydrogenated to form methoxyacetone, which is converted, inturn, with a Grignard compound which is obtained from a secondary butyl halide and magnesium. As a result, 2,3-dimethyl-1-methoxy-pentanol-(2) is formed. The last compound is, in the presence of a strongly acid agent, converted to 2,3-dimethyl-pentanal. The pentanal is condensed with formaldehyde in an alkaline medium to produce the desired end product.

A similar process, requiring 5 stages, is described in French Pat. No. 1,377,141. This method is also shown in Ann. Chim. (Rome) 53 (10), 1441-46 (1963). In this process, the starting materials are 3-methyl-pentanone-(2) and monochlorodimethyl ether.

These processes, as well as others in the prior art, require starting materials which are both expensive and difficult to obtain. Moreover, they frequently require complex and time consuming purification steps in order to obtain an end product of the purity necessary for the production of a drug or pharmaceutical.

Therefore, it is among the objects of this invention to provide a process by which the desired diol can be obtained (1) in high yield, (2) in a very pure form, (3) in a technically simple manner, and (4) from inexpensive starting materials.

The present invention prepares 2-methyl-2-sec.butyl 1,3-propanediol from 2-methyl-1-butene as the starting material.

In practicing this invention, the butene is hydroformylated with carbon monoxide and hydrogen in the presence of a first catalyst to form 3-methyl-pentanal. This compound is condensed with formaldehyde in the presence of a base to form alpha-sec. butylacrolein. The acrolein is partially hydrogenated in the presence of a second catalyst and the reaction product, 2,3-dimethyl-pentanal, is converted by treatment with formaldehyde into the desired diol. The conversion is carried out in the presence of an alkaline catalyst.

The starting 2-methyl-1-butene is readily available commercially. It is easily obtained by fractional distillation of the $C_5$ cut from naphtha cracking. Alternatively, 2-methylbutanol-(1) can be dehydrated to form this starting material. It is one of the advantages of the present process that no particular level of purity is required. The commercial grade of the methylbutene, which is about 96% pure, is entirely satisfactory.

The hydroformylation to 3-methylpentanal takes place with carbon monoxide and hydrogen in the presence of a cobalt or rhodium catalyst. Preferably, rhodium is used and the reaction is carried out at 70° to 150° C. and at 200 to 400 bar. It has been found advantageous to add an organic phosphine to the rhodium catalyst. Especially preferred is tri-n-butylphosphine or triphenylphosphine.

It has been found especially advantageous if the atomic ratio of rhodium and phosphorous is adjusted to a value of 1:10 to 1:30. It has also been found useful to separate the 3-methyl-pentanal from the catalyst by simple flash distillation at 200 mm Hg.

The condensation of the pentanal with formaldehyde is carried out in the presence of secondary amines. In particular, di-n-butylamine has proved suitable in this respect. It is preferably used in an amount of 0.5 to 5.0% by weight, based on the 3-methyl-pentanal present.

The formaldehyde is usually employed in the form of an aqueous solution. However, it is recognized that compounds which form formaldehyde under the conditions of the reaction may be used. For example, condensation and polymerization products of formaldehyde, such as trioxymethylene and paraformaldehyde are acceptable.

The reaction preferably takes place at 90° to 120° C. under atmospheric pressure. A solvent, such as cyclohexane or a higher alcohol, will not interfere with the reaction. However, its use is not essential. Moreover, the reaction can be carried out either continuously or in a batchwise manner.

After the reaction has proceeded for approximately one hour, the reaction mixture separates into phases. The desired crude alpha-sec. butyl acrolein is separated from the catalyst and the higher boiling compounds by flash distillation at 200 mm Hg.

The next step is to partially hydrogenate the aforementioned acrolein to form 2,3-dimethyl-pentanal. The addition of hydrogen takes place in the presence of suitable catalysts, such as palladium or platinum. These catalysts should preferably contain 0.1 to 10.0% by weight of metal, based on the total amount of catalysts, and are, for best results, supported on activated charcoal or aluminum oxide. The hydrogenation can advantageously be carried out in the liquid phase at 40° to 140° C. and 1 to 150 bar. Approximately 0.1 to 2.0% by weight of the catalyst based on the acrolein present has been found satisfactory.

The pentanal from the previous step is reacted directly with formaldehyde in the presence of strong bases such as aqueous sodium hydroxide. Here, too, the formaldehyde can be replaced by a compound which forms formaldehyde under the reaction conditions. The reaction is usefully carried out at 60° to 100° C. and the desired 2-methyl-2-sec. butyl-1,3-propanediol is produced after approximately 30 to 60 minutes. A particularly useful embodiment of the conversion provides a molar ratio of 2,3-dimethyl-pentanal, formaldehyde, and sodium hydroxide (in the form of a 30% aqueous solution) of 1 to 2.75 to 1.2.

Alternatively, the 2,3-dimethyl-pentanal can be reacted with formaldehyde to form the corresponding 2,3-dimethyl-[2-hydroxymethyl pentanale]. The formyl group is then hydrogenated to produce the desired diol.

The reaction mixture is distilled to separate the 2-sec. butyl-2-methyl-1,3-propandiol. The 2-methyl-2-sec. butyl-1,3-propane-diol is sufficiently pure so that it does not require any further treatment. It can be used for the production of various pharmaceuticals as it is produced from this reaction.

As may be apparent from the foregoing description, the present process has substantial advantages over the prior art. The desired diol is obtained in yields of at least 75% based upon the starting material, 2-methyl-1-butene. Furthermore, the process is technically very simple and requires no special materials or equipment. It can be carried out as a batch process or continuously as desired. Moreover, no costly and time consuming purification operations are required between the individual reaction stages. It is an important feature of the present invention that it is necessary only to separate the reaction products at each intermediate stage from the higher boiling point fractions and catalysts by a simple flash distillation operation. The final product is obtained in highly pure form by fractional distillation.

The following example illustrates the present invention without limiting it.

EXAMPLE (a) Preparation of 3-methylpentanal 500 g of an olefin consisting of 96.3% of 2-methyl-1-butene, 0.4% of 3-methyl-1-butene, 1.0% of 1-pentene, 2.0% of 2-pentene, 0.1% of 1-butene and 0.2% of n-pentane, 50 mg of rhodium (in the form of the 2-ethylhexanoate) and 2.9 g of tri-n-butyl phosphine are placed in a 2.1 liter volume high pressure vessel and reacted with an equimolar mixture of carbon monoxide and hydrogen at 130° C. and 260-270 bar. The reaction is complete after 3 hours. According to gas chromatography analysis the reaction product contains, after separation of the catalyst, 90.3% of 3-methylpentanal in addition to 7.0% of hydrocarbons and 2.7% of other, presumably aldehydic, components.

(b) Preparation of alpha-sec. butylacrolein 1000 g of crude 3-methylpentanal (90%) from a), 925 g of aqueous formaldehyde solution (30%) and 400 g of amyl alcohol are heated at 30° C. while stirring in a 5 liter steel autoclave. 28 g of di-n-butylamine is next added within 30 minutes. The mixture is then heated to 100° C. and after 60 minutes reaction at 100° C. is cooled and the phases are separated. As shown by gas chromatography analysis, the reaction mixture contains approximately 84% of alph-sec. butyl acrolein (without solvent). The higher boiling point components are separated by flash distillation at 97°-102° C./200 mm Hg. The yield is 96% referred to the 3-methyl-pentanal used, and is thus almost quantitative.

(c) Preparation of 2,3-dimethylpentanal 1000 g of crude alpha-sec. butyl acrolein (according to b)) is hydrogenated in a steel autoclave at a temperature of 100° C. and a hydrogen pressure of 20 bar, using 1% by weight of a Pd catalyst (5% by weight of Pd on activated charcoal) referred to the unsaturated aldehyde. When the addition of hydrogen is complete the pressure is released and the reaction mixture is filtered off from the catalyst. Gas chromatography analysis shows that the hydrogenation product consists of about 84% of 2,3-dimethylpentanal (without solvent).

(d) Preparation of 2-methyl-2-2-sec. butyl-1,3-propanediol 1000 g of crude 2,3-dimethyl-pentanal (gas chromatography analysis: 64% 2,3-dimethyl-pentanal, 29% amyl alcohol, 1% hydrocarbons 2% various aldehydes and 4% higher boiling point compounds) and 1423 g of 30% aqueous formaldehyde solution are placed in a vessel provided with a stirrer and heated to 40° C. while stirring. 828 g of a 30% aqueous caustic soda solution is then added dropwise within 30 minutes. The temperature of the resulting exothermic reaction is kept at 80° C. by cooling. When all of the caustic soda has been added the mixture is stirred for a further 15 minutes at 80° C. and is then cooled to 40° C. following which the phases are separated. In order to purify the diol, the organic phase is fractionally distilled. A main fraction containing 99.8% of 2-methy-2-sec. butyl-1,3-propanediol is obtained at a pressure of 30 mm Hg and at 155° C. The yield of pure 2-methyl-2-sec. butyl-1,3-propanediol is 75% based on the 2-methyl-1-butene used.

Although only a single specific embodiment of the present invention has been expressly disclosed, it is, nonetheless, to be broadly construed and not to be limited except by the character of the claims appended hereto.

What we claim is:

1. A process for the preparation of 2-methyl-2-sec. butyl-1,3-propanediol comprising
   hydroformylating 2-methyl-1-butene with carbon monoxide and hydrogen in the presence of a first catalyst to form the substance 3-methyl-pentanal,
   separating said methyl pentanal from said first catalyst by flash distillation,
   condensing said substance with formaldehyde, or a compound which forms formaldehyde under the conditions of condensation in a basic medium to form alpha-sec. butyl-acrolein,
   separating said acrolein from said basic medium by flash distillation,
   partially hydrogenating said acrolein in the presence of a second catalyst to form the material 2,3-dimethylpentanal, and
   converting said material into said diol by treatment with formaldehyde, or a compound which forms formaldehyde under the conditions of conversion, in the presence of a strong base as a third catalyst.

2. A process according to claim 1 wherein said first catalyst is cobalt or rhodium and said hydroformylation is carried out at 70° to 150° C. and 200 to 400 bar.

3. A process according to claim 2 wherein said first catalyst is rhodium and said hydroformylation is carried out in the presence of at least one organic phosphine, there being 10 to 30 gram atoms of phosphorous per gram atom of rhodium.

4. A process according to claim 1 wherein said condensation is carried out at 90° to 120° C. in the presence of 0.5 to 5.0% by weight of secondary amines based on said substance.

5. A process according to claim 1 wherein said second catalyst is palladium or platinum and said partial hydrogenation is carried out at 40° to 140° C. and 1 to 150 bar.

6. A process according to claim 5 wherein said second catalyst is on activated charcoal or aluminium oxide as a support.

7. A process according to claim 1 wherein said conversion is carried out at 60° to 100° C.

8. A process according to claim 2 wherein said condensation is carried out at 90° to 120° C. in the presence of 0.5 to 5.0% by weight of secondary amines based on said substance, said second catalyst is palladium or platinum, said partial hydrogenation is carried out at 40° to 140° C. and 1 to 150 bar, and said conversion is carried out at 60° 100° C.

9. A process according to claim 3 wherein said phosphine is tri-n-butyl phosphine or triphenyl phosphine.

10. A process according to claim 4 wherein said secondary amine is di-n-butyl amine.

11. A process according to claim 1 wherein said compound is trioxymethylene or paraformaldehyde.

12. A process according to claim 5 wherein said second catalyst contains 0.1 to 10.0% by weight of metal based on the total weight of said second catalyst.

13. A process according to claim 12 wherein said second catalyst comprises 0.1 to 2.0% by weight based on said acrolein.

14. A process according to claim 7 wherein said conversion is carried out for 30 to 60 minutes.

15. A process according to claim 1 wherein the molar ratio of said material, said formaldehyde used in said conversion, and said strong base is about 1 to 2.75 to 1.2.

16. A process according to claim 1 wherein said second catalyst is palladium.

17. A process according to claim 1 wherein said dimethyl pentanal is reacted with formaldehyde to form 2,3-dimethyl-2-hydroxymethyl-pentanal which is then hydrogenated to form said diol.

18. The process of claim 1 wherein said dimethyl pentanal is separated from said second catalyst before said converting.

* * * * *